United States Patent

Murayama et al.

Patent Number: 5,204,461
Date of Patent: Apr. 20, 1993

[54] PROCESS FOR PREPARING (1'R,3S)-3-(1'-HYDROXYETHYL)-AZETIDIN-2-ONE AND DERIVATIVES THEREOF

[75] Inventors: Toshiyuki Murayama; Takashi Miura; Toyohiko Kobayashi, all of Tokyo, Japan

[73] Assignee: Takasago International Corporation, Tokyo, Japan

[21] Appl. No.: 789,604

[22] Filed: Nov. 8, 1991

[30] Foreign Application Priority Data

Nov. 8, 1990 [JP] Japan .................. 2-301016

[51] Int. Cl.$^5$ .................. C07D 205/08; C07B 43/06
[52] U.S. Cl. .................. 540/362; 540/200
[58] Field of Search .................. 540/362, 200

[56] References Cited

U.S. PATENT DOCUMENTS 5,037,974  8/1991  Loewe .................. 540/200

OTHER PUBLICATIONS

Kobayashi, JACS 103, 2406-8 (1981).

*Primary Examiner*—Mark L. Berch
*Attorney, Agent, or Firm*—Sughrue, Mion, Zinn, Macpeak & Seas

[57] ABSTRACT

A process for preparing (1'R,3S)-3-(1'-hydroxyethyl)-azetidin-2-one or a derivative thereof represented by formula (I):

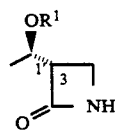

(I)

wherein $R^1$ represents a hydrogen atom or a hydroxyl-protective group, is disclosed, comprising reacting (2S,3R)-2-aminomethyl-3-hydroxybutyric acid or a derivative thereof represented by formula (II):

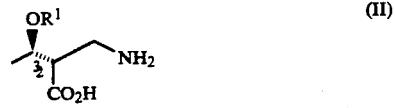

(II)

wherein $R^1$ is as defined above, with a sulfenamide represented by formula (III):

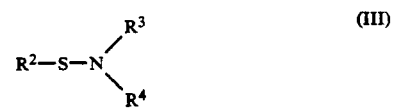

(III)

wherein $R^2$ represents

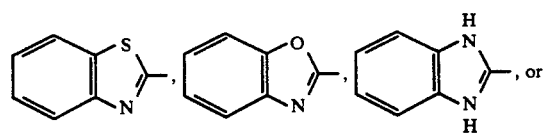

, or

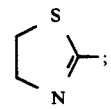

and $R^3$ and $R^4$ each represent a hydrogen atom or a cyclic or acyclic hydrocarbon group, provided that they do not simultaneously represent a hydrogen atom, or $R^3$ and $R^4$ are taken together with the adjacent nitrogen atom to form a heterocyclic group, and triphenylphosphine. The reaction yield is high, and the sulfenamide (III) used as a lactamization reagent is cheap and can be recovered after the reaction.

4 Claims, No Drawings

PROCESS FOR PREPARING (1'R,3S)-3-(1'-HYDROXYETHYL)-AZETIDIN-2-ONE AND DERIVATIVES THEREOF

FIELD OF THE INVENTION

This invention relates to a process for preparing (1'R,3S)-3-(1'-hydroxyethyl)-azetidin-2-one or a derivative thereof represented by formula (I):

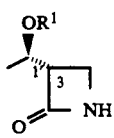

wherein $R^1$ represents a hydrogen atom or a hydroxyl-protective group, which is useful as an intermediate for synthesizing carbapenem antibiotics exemplified by thienamycin.

BACKGROUND OF THE INVENTION

Carbapenem antibiotics represented by thienamycin have attracted attention as medicines because of their broad antimicrobial spectra.

Various processes for preparing carbapenem antibiotics have been reported, e.g., in Kametani, et al., *Heterocycles*, Vol. 17, pp. 463-506 (1982) and Shibuya, et al., *Yuki Gosei Kagaku*, Vol. 41, p. 62 (1983). Among the known processes, a process using(1'R,3R,4R)-4-acetoxy-3-(1'-hydroxyethyl)-azetidin-2-one or a derivative thereof represented by formula (IV):

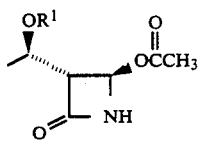

wherein $R^1$ is as defined above, as an intermediate is particularly advantageous in that the compound of formula (IV) is reactive with various nucleophilic agents.

The intermediate compound of formula (IV) can be synthesized by, for example, the process disclosed in JP-A-2-134349 (corresponding to U.S. Pat. No. 4,981,992 and European Patent 369,691A) (the term "JP-A" as used herein means an "unexamined published Japanese patent application"), which comprises acetoxylation of a (1'R,3S)-3-(1'-hydroxyethyl)azetidin-2-one derivative (I-B) as illustrated in the following reaction scheme.

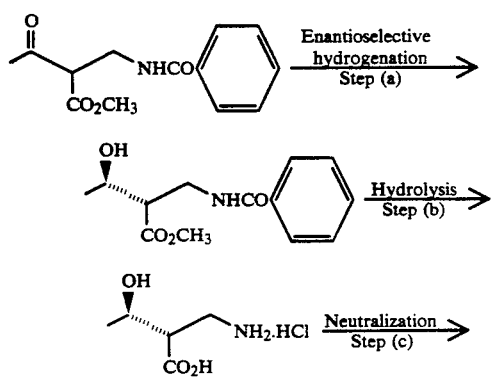

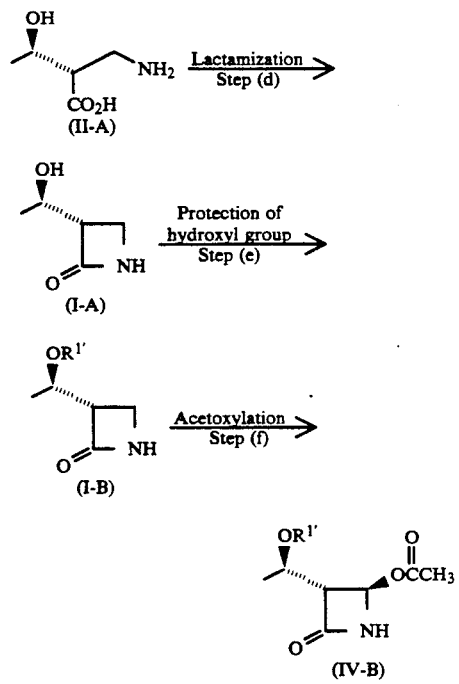

wherein $R^1$, represents a hydroxyl-protective group.

Known techniques for lactamization of a β-amino acid to obtain an azetidin-2-one skeleton as in Step (d) in the above reaction scheme include (1) utilization of Grignard reaction (see Robert W. Holley, et al., *J. Am. Chem. Soc.*, Vol. 71, pp. 2124-2129 (1949), Scott Searrles, et al., *Chemistry and Industry*, p. 2097 (1964), and Leonhard Birkofer, et al., *Ann. Chem.*, pp. 2195-2200 (1975)), (2) treatment with thionyl chloride-tertiary amine (see F. F. Blicks, et al., *J. Org. Chem.*, Vol. 23, pp. 1102-1107 (1958)), (3) treatment with N,N'-dicyclohexylcarbodiimide (see D. G. Melillo, et al., *Tetrahedron Lett.*, Vol. 21, pp. 2783-2786 (1980)), (4) use of a two liquid-liquid phase transfer system in which methylene chloride/$H_2O$: tetrabutylammonium hydrogensulfate is used as a phase transfer agent, and methanesulfonyl chloride and potassium hydrogen-carbonate are used as a cyclizing agent (see Yutaka Watanabe, et al., *Chemistry Letters*, pp. 443-444 (1981)), (5) treatment with 2-chloro-1-methylpyridium iodide (see Huamin Huang, et al., *Chemistry Letters*, pp. 1465-1466 (1984)), (6) treatment with bis-(5'-nitro-2'-pyridyl)-2,2,2-trichloroethylphosphinic acid (see Sunggak Kim, et al., *Tetrahedron Lett.*, Vol. 28, pp. 2735-2736 (1987)), (7) treatment with diphenylphosphinic acid chloride (see Sunggak Kim, et al., *J. Chem. Soc., Chem. Commun.*, pp. 1242-1243 (1988)), (8) treatment with a heterocyclic disulfide (e.g., 2,2'-dipyridyl disulfide, 2,2'-dibenzothiazolyl disulfide, and 2,2'-dibenzimidazolyl disulfide) and triphenylphosphine in the presence of an alkylnitrile [see JP-A-57-77670 (corresponding to European Patent 51,234B)], and (9) treatment with methanesulfonyl chloride and sodium hydrogencarbonate [see JP-A-2-17175 (corresponding to European Patent 343,716A)].

According to these processes, the yield of the lactam often depends on the structure of the reactant, β-amino acid. Process (8) mentioned above is adopted in the conventional techniques for cyclizing(2S,3R)-2- aminomethyl-3-hydroxybutyric acid or a derivative thereof to obtain the corresponding lactam disclosed in David A. Evans, et al., *Tetrahedron Lett.*, Vol. 27, No. 41, pp. 4961–4964 (1986), JP-A-63-297360 (corresponding to U.S. Pat. No. 4,927,507 and European Patent 290,385A), and JP-A-2-134349. More specifically, the reactant is treated with 2,2'-dipyridyl disulfide. However, 2,2'-dipyridyl disulfide is not only very expensive but unable to be recovered after the reaction. Hence, it has been demanded to develop a process for lactamization in good yield at low cost.

On the other hand, a sulfenamide represented by formula (III):

 (III)

wherein $R^2$ represents

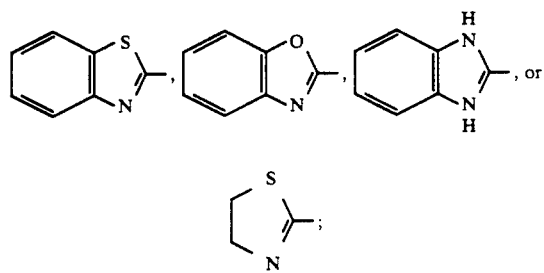

and $R^3$ and $R^4$ each represent a hydrogen atom or a cyclic or acyclic hydrocarbon group, provided that they do not simultaneously represent a hydrogen atom, or $R^3$ and $R^4$ are taken together with the adjacent nitrogen atom to form a heterocyclic group, which is used as a reagent for lactamization in the present invention, is known to react with a thiazolinoazetidinone derivative in a water-containing organic solvent in the presence of an acid to open the thiazolyl ring thereof to obtain an intermediate for synthesizing cephalosporin type antibiotics as disclosed, e.g., in JP-A-59-44356 (corresponding to U.S. Pat. No. 4,622,178 and European Patent 117,875B). However, there is no case reported in which such a sulfenamide is used in synthesis of lactams.

SUMMARY OF THE INVENTION

In the light of the above situation, the inventors have conducted extensive investigations. As a result, it has now been found that the (1'R,3S)-3-(1'-hydroxyethyl)-azetidin-2-one or a derivative thereof represented by formula (I) can be prepared with industrial advantages by using the above-mentioned sulfenamide represented by formula (III) and triphenylphosphine as a reagent for lactamization. The present invention has been completed based on this finding.

That is, the present invention provides a process for preparing (1'R,3S)-3-(1'-hydroxyethyl)-azetidin-2-one or a derivative thereof represented by formula (I), which comprises reacting (2S,3R)-2-aminomethyl-3-hydroxybutyric acid or a derivative thereof represented by formula (II):

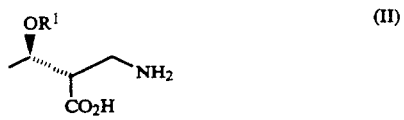

wherein $R^1$ is as defined above, with a sulfenamide represented by formula (III) shown above and triphenylphosphine.

DETAILED DESCRIPTION OF THE INVENTION

The starting compound of formula (II) which can be used in the process of this invention is a known compound as stated above. The compound of formula (II) wherein $R^1$ is a hydrogen atom, i.e., compound (II-A), can easily be prepared, for example, in accordance with the reaction routes of from Step (a) to Step (c) in the above-illustrated scheme.

Compound (II-A) with its hydroxyl group protected, i.e., compound (II-B), is also used as a starting compound for lactamization. Protective groups for a hydroxyl group include tri-substituted silyl groups, e.g., a t-butyldimethylsilyl group, an n-propyldimethylsilyl group, an isopropyldimethylsilyl group, and a triethylsilyl group. Such a protective group can be introduced into compound (II-A) by reacting compound (II-A) with a chloride of the tri-substituted silyl group in a solvent, e.g., acetonitrile, propionitrile, tetrahydrofuran, N,N-dimethylformamide, and ethyl acetate, in the presence of a base, e.g., pyridine, 2,6-dimethylpyridine, imidazole, triethylamine, and diisopropylethylamine. The tri-substituted silyl chloride is used in an amount of at least 1.0 mole, and preferably from about 1.3 to 2.0 mole, per mole of compound (II-A). The base is suitably used in an equimolar amount to the tri-substituted silyl chloride. The reaction temperature and time are not particularly critical and are subject to variation depending on the species of compound (II-A). In a preferred embodiment, the reaction is usually carried out at a temperature of from 0° to 80° C., and preferably at room temperature, for a period of from 1 to 24 hours.

A (1'R,3S)-3-(1'-hydroxyethyl)-azetidin-2-one derivative with the hydroxyl group thereof protected (compound I-B) which is obtained by lactamization of the above obtained compound (II-B) is advantageous because protection of the hydroxyl group is needed in the subsequent reactions leading to carbapenem antibiotics.

The present invention is characterized by using a sulfenamide of formula (III) and triphenylphosphine as a reagent for lactamization.

In formula (III), $R^3$ and $R^4$ each specifically represent a hydrogen atom; a straight chain or branched lower alkyl group, e.g., a methyl group, an ethyl group, an isopropyl group, and a t-butyl group; or a cyclic alkyl group, e.g., a cyclopentyl group and a cyclohexyl group; or $R^3$ and $R^4$ are taken together with the nitrogen atom to form a heterocyclic group, e.g., a 4-morpholinyl group, a 1-piperidinyl group, and a 1-pyrrolidinyl group.

Most of these sulfenamide compounds of formula (III) are known per se and can be prepared by the process disclosed in E. L. Carr, et al., *J. Org. Chem.*, Vol. 14, p. 921 (1949). For example, N-cyclohexyl-2-thiazolinylsulfenamide represented by formula (III) wherein $R^2$ is

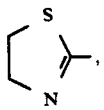

$R^3$ is a hydrogen atom, and $R^4$ is a cyclohexyl group is obtainable by dropwise addition of a solution of 2-mercaptothiazoline in a sodium hydroxide aqueous solution and a sodium hypochlorite aqueous solution to a mixture of cyclohexylamine and water. Likewise, other sulfenamide compounds are easily prepared by reacting a solution of the corresponding mercaptan compound in a sodium hydroxide aqueous solution and a sodium hypochlorite aqueous solution with a mixture of the corresponding amine and water.

The sulfenamide of formula (III) is suitably used in an amount of at least 1.0 mole, and preferably from about 1.0 to 1.3 mole, per mole of the starting compound of formula (II), though more or less variable depending on the reaction conditions.

Triphenylphosphine is preferably used in an approximately equimolar amount to the sulfenamide of formula (III).

Solvents which can be used in the reaction include alkylnitriles, e.g., acetonitrile and propionitrile; ethers, e.g., diethyl ether, tetrahydrofuran, and dioxane; N,N-dimethylformamide; dimethyl sulfoxide; isopropanol; aromatic hydrocarbons, e.g., benzene and toluene; and cyclohexane.

Silylation of from compound (II-A) to compound (II-B) and subsequent lactamization of compound (II-B) may be performed in one reaction vessel. In this case, it is preferable to use acetonitrile as a common solvent for achieving smooth progress of the reaction and a high yield. While silylation also results in by-production of a compound wherein the carboxyl group of compound (II-B) is also protected with a silyl group, the silyl group protecting the carboxyl group can be removed by treating the compound with methanol prior to lactamization.

The reaction temperature and time are not particularly limited and are subject to variation according to the species of the compound (II). In general, the reaction is effected at a temperature of from room temperature to the refluxing temperature of the solvent used, and preferably from 70° to 80° C., for a period of from 1 to 24 hours.

The starting compound of formula (II) is used in a concentration of from about 0.001 mole/l to 1 mole/l, and preferably from about 0.01 mole/l to 0.1 mole/l, in the reaction system. If the concentration of the starting compound is too high, the yield of the product (I) is reduced.

Other reaction conditions are subject to variation according to the species of the reactants. In one of preferred embodiments, the reaction advantageously proceeds to attain a good yield by adding a solution of triphenylphosphine in an appropriate solvent (e.g., acetonitrile and toluene) dropwise to a suspension of the starting compound (II) and the sulfenamide (III) in a suspension medium over a period of from about 5 minutes to 60 minutes while refluxing.

After completion of the reaction, the reaction mixture is worked up in a known manner, such as distillation under reduced pressure to remove the solvent, followed by column chromatography, to isolate the desired compound of formula (I) and to recover the starting compound of the sulfenamide (III), i.e., a mercaptan compound.

The present invention is now illustrated in greater detail by way of Reference Examples and Examples, but it should be understood that the present invention is not construed as being limited thereto. In these examples, all the percents are by weight unless otherwise indicated.

REFERENCE EXAMPLE 1

Synthesis of N-Cyclohexyl-2-thiazolinylsulfenamide

A mixture of 12.3 g (124 mmole) of cyclohexylamine and 30 ml of water was thoroughly stirred in an ice bath, and 30 ml of a 1N sodium hydroxide aqueous solution having dissolved therein 3.57 g (30 mmole) of 2-mercaptothiazoline and 22.3 ml (30 mmole) of a 10% sodium hypochlorite aqueous solution were simultaneously added thereto dropwise. After allowing the mixture to react at room temperature for 1 hour, the reaction mixture was filtered with suction. The resulting solid was washed with water and dried under reduced pressure to obtain 5.61 g (26 mmole) of the titled compound in a percent yield of 87%.

EXAMPLE 1

In 19 ml of acetonitrile were suspended 134 mg (1.01 mmole) of (2S,3R)-2-aminomethyl-3-hydroxybutyric acid (II-A) and 251 mg (1.05 mmole) of N-t-butyl-2-benzothiazole sulfenamide (III) synthesized from N-t-butylamine and 2-mercaptobenzothiazole in the same manner as in Reference Example 1, and the suspension was heated at reflux. A solution of 275 mg (1.05 mmole) of triphenylphosphine in 0.5 ml of toluene was added dropwise to the suspension under reflux over 25 minutes. After continuing refluxing for 2 hours, the reaction mixture was concentrated under reduced pressure, and the residue was purified by silica gel column chromatography (silica gel: 20 g; developing solvent: methylene chloride/ethyl acetate/methanol=10:10:1 by volume) to obtain 95 mg (0.83 mmole) of (1'R,3S)-3-(1'-hydroxyethyl)-azetidin-2-one (I-A) in a percent yield of 82%.

The IR, NMR and mass spectra of the product agreed with those of a standard sample.

EXAMPLES 2 TO 6

(1'R,3S)-3-(1'-hydroxyethyl)-azetidin-2-one (I-A) was synthesized in the same manner as in Example 1 under reaction conditions shown in Table 1 below in yield and percent yield shown. In each case, acetonitrile was used as a reaction solvent, and toluene was used as a solvent for triphenylphosphine. The reaction results are shown in Table 1.

TABLE 1

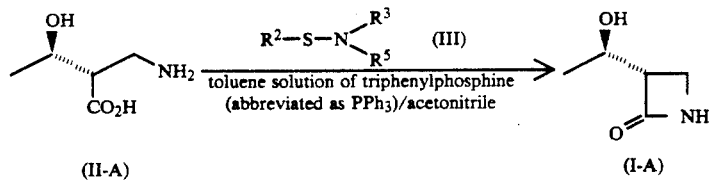

| Example No. | Amount of (II-A) (mg) | (III) Kind | (III) Amount (mg) | Solvent Amount (Acetonitrile) (ml) | Amount of PPh₃ (mg) | Solvent Amount of PPh₃ (Toluene) (ml) | Time of PPh₃ Dropwise Addition (min) | Refluxing Time (hr) | Yield of (I-A) (mg) | Percent Yield of (I-A) (%) |
|---|---|---|---|---|---|---|---|---|---|---|
| 2 | 133 (1.00)* | benzothiazole-SN-morpholine | 277 (1.07) | 19 | 275 (1.05) | 0.5 | 25 | 2 | 92 (0.80) | 80 |
| 3 | 133 (1.00) | benzoxazole-SNHC(CH₃)₃ | 233 (1.05) | 19 | 275 (1.05) | 0.6 | 30 | 1 | 69 (0.60) | 60 |
| 4 | 133 (1.00) | benzimidazole-SNHC(CH₃)₃ | 232 (1.05) | 19 | 275 (1.05) | 0.6 | 30 | 9 | 102 (0.89) | 89 |
| 5 | 133 (1.00) | thiazoline-SNHC(CH₃)₃ | 204 (1.07) | 19 | 275 (1.05) | 0.6 | 40 | 9 | 112 (0.97) | 97 |
| 6 | 133 (1.00) | thiazoline-SNH-cyclohexyl | 226 (1.05) | 19 | 275 (1.05) | 0.6 | 40 | 24 | 106 (0.92) | 92 |

Note: Values in the parentheses indicate millimole.

EXAMPLE 7

In 10 ml of acetonitrile were suspended 266 mg (2.00 mmole) of (2S,3R)-2-aminomethyl-3-hydroxybutyric acid (II-A) and 300 mg (3.02 mmole) of triethylamine, and the suspension was heated at 70° C. with stirring. A solution of 453 mg (3.00 mmole) of t-butyldimethylsilyl chloride in 4 ml of acetonitrile was dropwise added thereto over 10 minutes, followed by stirring for 2.5 hours. To the reaction mixture was added 3.5 ml of methanol, followed by further stirring at room temperature for 2.5 hours. The solvent was removed by distillation under reduced pressure, and to the residue were added 476 mg (2.00 mmole) of N-t-butyl-2-benzothiazole sulfenamide (III) and 40 ml of acetonitrile, followed by heating to 70° C. To the solution was added dropwise a solution of 524 mg (2.00 mmole) of triphenylphosphine in 10 ml of acetonitrile over 20 minutes. After completion of the dropwise addition, the stirring was continued for 5 minutes at 70° C. The reaction mixture was concentrated under reduced pressure, and the residue was purified by silica gel column chromatography (silica gel: 60 g; developing solvent: hexane/ethyl acetate=7:3 to 1:1 by volume) to obtain 359 mg (1.56 mmole) of (1′R,3S)-3-(1′-t-butyldimethylsilyloxyethyl)-azetidin-2-one (I-B) in a percent yield of 78%.

The IR, NMR and mass spectra of the product agreed with those of an authentic sample.

The compound represented by formula (II) is a derivative of a β-amino acid and can be converted to a compound having an azetidin-2-one skeleton by the reaction according to the present invention. This reaction is based on the premise that a sulfenamide (III) and triphenylphosphine act as a cyclizing agent in the lactamization of an ω-amino acid. In order to prove the premise, basic experiments were conducted in which γ-butyrolactam or δ-valerolactam was produced from γ-aminobutyric acid or δ-aminovaleric acid, respectively, as the starting ω-amino acid in accordance with the procedures of Example 1. The scheme of reactions involved are illustrated below.

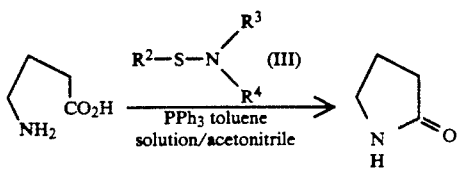

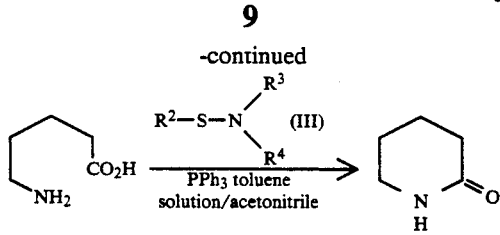

REFERENCE EXAMPLE 2

In 35 ml of acetonitrile were suspended 209 mg (2.03 mmole) of γ-aminobutyric acid d 455 mg (2.11 mmole) of N-cyclohexyl-2-thiazolinyl sulfenamide (III), and the suspension was heated at reflux. A solution of 550 mg (2.10 mmole) of triphenylphosphine in 0.6 ml of toluene was added dropwise thereto over 10 minutes while heat-refluxing. After the refluxing was continued for about 27 hours, the reaction mixture was cooled to room temperature and purified by silica gel column chromatography (silica gel: 20 g; developing solvent: ethyl acetate/methanol=9:1 by volume) to obtain 159 mg (1.87 mmole) of γ-butyrolactam in a percent yield of 92%.

REFERENCE EXAMPLE 3

In the same manner as in Reference Example 2, 107 mg (1.04 mmole) of γ-aminobutyric acid was lactamized with 250 mg (1.05 mmole) of N-t-butyl-2-benzothiazole sulfenamide (III) and 275 mg (1.05 mmole) of triphenylphosphine to obtain 74 mg (0.87 mmole) of γ-butyrolactam in a percent yield of 84%.

REFERENCE EXAMPLE 4

In the same manner as in Reference Example 2, 235 mg (2.01 mmole) of δ-aminovaleric acid was lactamized with 435 mg (2.01 mmole) of N-cyclohexyl-2-thiazolinylsulfenamide (III) and 528 mg (2.01 mmole) of triphenylphosphine to obtain 191 mg (1.93 mmole) of δ-valerolactam in a percent yield of 96%.

REFERENCE EXAMPLE 5

In the same manner as in Reference Example 2, 117 mg (1.00 mmole) of δ-aminovaleric acid was lactamized with 250 mg (1.05 mmole) of N-t-butyl-2-benzothiazole sulfenamide (III) and 275 mg (1.05 mmole) of triphenylphosphine to obtain 84 mg (0.85 mmole) of δ-valerolactam in a percent yield of 85%.

According to the present invention, (1'R,3S)-3-(1'-hydroxyethyl)-azetidin-2-one or a derivative thereof useful as a synthetic intermediate for carbapenem antibiotics can be prepared in a satisfactory yield at a low cost by using a reaction reagent which is cheap and also can be recovered after the reaction. The use of the sulfenamide as a reaction reagent for lactamization was developed for the first time by the present inventors and is also applicable to production of γ-lactams or δ-lactams from the corresponding γ-amino acids or δ-lactams amino acids as well as production of azetidinone derivatives other than (1'R,3S)-3-(1'-hydroxyethyl)-azetidin-2-one of the present invention.

While the invention has been described in detail and with reference to specific examples thereof, it will be apparent to one skilled in the art that various changes and modifications can be made therein without departing from the spirit and scope thereof.

What is claimed is:

1. A process for preparing (1'R,3S)-3-(1'-hydroxyethyl)-azetidin-2-one or (1'R,3S)-3-(1'-hydroxyethyl)-azetidin-2-one whose hydroxyl group has been protected represented by formula (I):

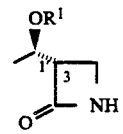

wherein $R^1$ represents a hydrogen atom or a hydroxyl-protective group, which comprises reacting (2S,3R)-2-aminomethyl-3-hydroxybutyric acid or (2S,3R)-2-aminomethyl-3-hydroxybutyric acid whose hydroxyl group has been protected represented by formula (II):

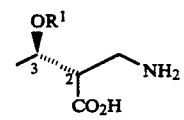

wherein $R^1$ is as defined above, with a sulfenamide represented by formula (III):

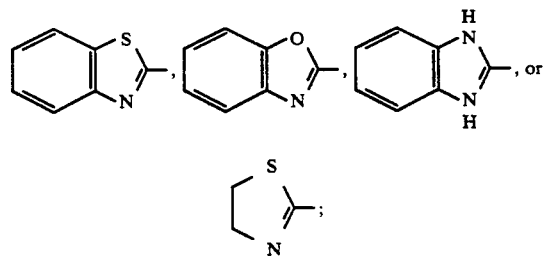

wherein $R^2$ represents

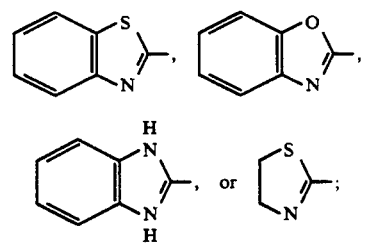

and $R^3$ and $R^4$ each represent a hydrogen atom or a cyclic or acyclic hydrocarbon group, provided that they do not simultaneously represent a hydrogen atom, or $R^3$ and $R^4$ are taken together with the adjacent nitrogen atom to form a 4-morpholinyl group, a 1-piperidinyl group or a 1-pyrrolidinyl group, and triphenylphosphine.

2. A process as in claim 1, wherein said sulfenamide represented by formula (III) is used in an amount of at least 1.0 mole per mole of said (2S,3R)-2-aminomethyl-3-hydroxybutyric acid or (2S,3R)-2-aminomethyl-3-hydroxybutyric acid whose hydroxyl group has been protected represented by formula (II).

3. A process as in claim 1, wherein said triphenylphosphine is used in an approximately equimolar amount to said sulfenamide represented by formula (III).

4. A process as in claim 1, wherein said hydroxyl group which has been protected is protected with a t-butyldimethylsilyl group, an n-propyldimethylsilyl group, an isopropyldimethylsilyl group or a triethylsilyl group.

* * * * *